United States Patent [19]

Stephens et al.

[11] Patent Number: 4,514,278
[45] Date of Patent: Apr. 30, 1985

[54] TRACE WATER SENSOR

[75] Inventors: James B. Stephens, LaCrescenta; Mary M. Yang, Berkeley; Eric G. Laue, San Marino, all of Calif.

[73] Assignee: The United States of America as represented by the Administrator of the National Aeronautics and Space Administration, Washington, D.C.

[21] Appl. No.: 457,992

[22] Filed: Jan. 14, 1983

[51] Int. Cl.³ ............................................. G01N 27/46
[52] U.S. Cl. .................................. 204/430; 204/1 T; 73/336.5
[58] Field of Search .............. 204/430, 1 W; 73/336.5

[56] References Cited

U.S. PATENT DOCUMENTS

| 1,383,233 | 6/1921 | Parsons et al. | 73/336.5 |
| 2,359,278 | 10/1944 | Allen et al. | 73/336.5 |
| 2,908,623 | 10/1959 | Doring | 204/196 |
| 2,993,853 | 7/1961 | Berry | 204/430 |
| 3,001,918 | 9/1961 | Czuha | 204/1 W |
| 3,240,693 | 3/1966 | Gardner | 204/430 |
| 3,683,243 | 8/1972 | Rockliff | 73/336.5 |
| 3,954,590 | 5/1976 | Czuha | 204/430 |
| 4,083,765 | 4/1978 | Lawson | 204/430 |
| 4,210,508 | 7/1980 | Bergson | 204/430 |
| 4,429,343 | 1/1984 | Freud | 73/336.5 |

FOREIGN PATENT DOCUMENTS

| 2644164 | 4/1977 | Fed. Rep. of Germany | 204/1 W |
| 67149 | 11/1957 | France | 73/336.5 |
| 139029 | 5/1979 | U.S.S.R. | 73/336.5 |

Primary Examiner—T. Tung
Attorney, Agent, or Firm—Paul F. McCaul; John R. Manning; Thomas H. Jones

[57] ABSTRACT

A solid electrolytic type hygrometer is described, which operates with high reliability while providing rapid and sensitive response. A gold foil electrode (16) is wrapped about a hollow glass cylinder (18), a sheet (12) of hygroscopic-electrolytic material is wrapped about the foil, and a wire (14) is wound around the outside of the electrolytic sheet. Moisture passing between wire turns can be absorbed by the electrolytic material (12), and then dissociated by current passed by the electrodes (14, 16) through the electrolytic material. The cylinder has a slit (20) extending along its length, to allow resilient expansion to press the sheet of electrolytic material firmly against the electrodes. The wire turns lie against one another to cause rapid dissociation of moisture throughout the electrolytic material. Additional guard wires (42, 44, FIG. 2) lie at opposite ends of the electrolytic sheet, and currents pass through them to avoid moisture buildup at the ends of the main wire coil. The electrical current through the sheet or membrane is proportional to the partial pressure of the water-vapor.

5 Claims, 5 Drawing Figures

4,514,278

TRACE WATER SENSOR

ORIGIN OF THE INVENTION

The invention described herein was made in the performance of work under a NASA Contract and is subject to the provisions of Section 305 of the National Aeronautics and Space Act of 1958, Public Law 85-568 (72 Stat. 435; 42 USC 2457).

BACKGROUND OF THE INVENTION

A hygrometer capable of operating under a wide range of temperature and pressure conditions can be constructed by using a sheet of solid hygroscopic-electrolyte material and placing electrodes in contact with opposite faces of this sheet. One electrode has numerous openings through which moisture can pass to be absorbed by the electrolytic sheet. When a voltage is applied between the electrodes, the current electrolyzes the moisture to gaseous hydrogen and oxygen. The amount of current is a direct measure of the moisture which has been absorbed. Thus, moisture can be absorbed over a period of time and a voltage then suddenly applied, or the device can be operated under steady state conditions. A hygrometer of this type is described in U.S. Pat. No. 4,083,765 by Lawson.

Several problems arise in constructing and operating this type of hygrometer. One problem is providing a relatively simple and rugged arrangement for applying electrodes to the electrolytic sheet and maintaining good contact of the electrodes therewith during slight expansion and contraction of the electrolytic sheet as it gains and looses moisture. Another problem is maintaining the electrode that has openings therein, in contact with the electrolytic sheet without considerable gaps in such contact, to assure that considerable current passes through all areas of the sheet. Still another problem is avoiding fringing effects near the edges of the sheets, where moisture may be absorbed but through which it is difficult to pass current. A solid electrolytic hygrometer which avoided these problems would therefore be of considerable value.

SUMMARY OF THE INVENTION

In accordance with one embodiment of the present invention, a moisture sensor is provided which is reliable and which has a fast and accurate response. The moisture sensor includes a layer of hygroscopic-electrolytic material with electrodes disposed on opposite thereof to which a voltage can be applied, to pass a current through the layer that indicates moisture absorbed therein. The layer and electrodes can be supported by wrapping them tightly about a tubular frame, and the tubular frame can have a slit therein to enable it to resiliently expand to press the electrolytic layer firmly against the electrodes.

The exposed electrode through which moisture passes to reach the electrolytic layer, can include multiple wire portions extending parallel to one another, such as wire turns about the tubular frame. Adjacent wire like segments leave a gap that is much less than half the diameter of the wire. Moisture reaches the wire surface and migrates along the surface to the electrolyte layer, so that only an extremely small gap is necessary between adjacent wire portions. An end effect, wherein moisture at an end of the electrolytic layer is not rapidly electrolyzed because one of the electrodes cannot extend to the very edge of the layer, is avoided by providing guard electrodes at the edges of the electrolytic layer.

The novel features of the invention are set forth with particularity in the appended claims. The invention will be best understood from the following description when read in conjunction with the accompanying drawings.

DESCRIPTION OF THE PREFERRED EMBODIMENT

Figure 1:
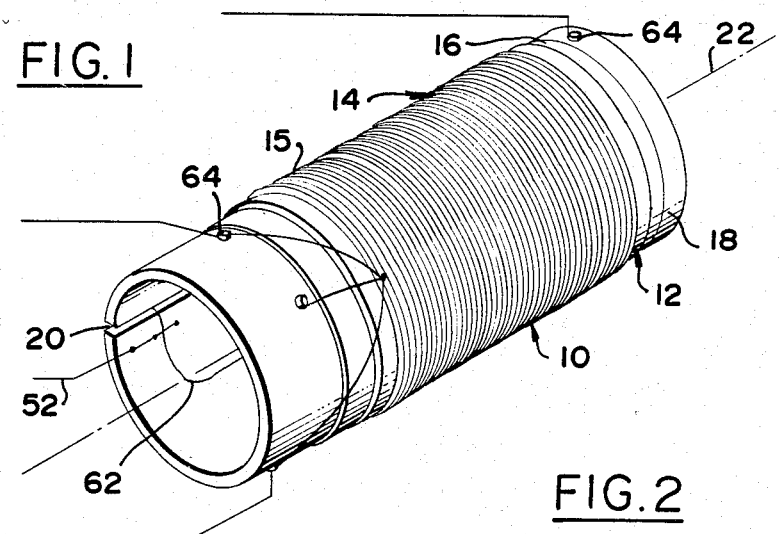
FIG. 1 is a perspective view of a moisture sensor constructed in accordance with the present invention.

FIG. 1 illustrates a moisture sensor device or hygrometer 10 that can detect small quantities of water that reach its outside surface. The hygrometer includes a layer or sheet of hygroscopic-electrolytic material 12 which can absorb water, a pair of primary electrodes 14, 16 disposed against the opposite surfaces of the electrolytic layer 12, and a frame 18 that supports the electrodes and electrolytic layer. The frame 18 is a tube of material such as glass, with a slot 20 therein that extends parallel to the axis 22 of the tubular frame. The inner electrode 16 is a sheet gold foil wrapped about the outside of the tubular frame 18. The electrolytic layer 12 is wrapped about the gold foil electrode 16. The outer electrode 14 is a gold-plated nickel wire that is tightly wound in a close helix about the electrolytic layer 12.

Figure 3:
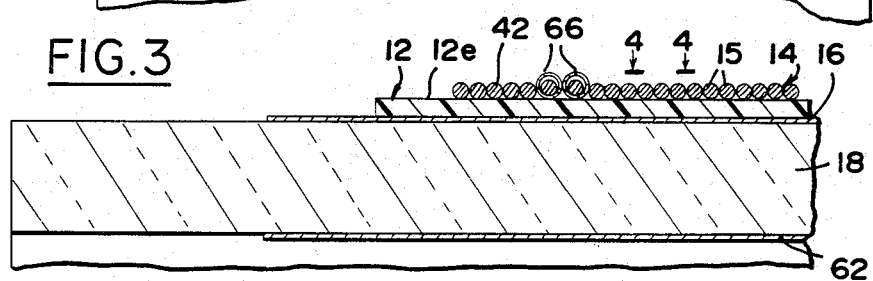
FIG. 3 is an enlarged sectional view of a portion of the sensor of FIG. 1.

Moisture can pass through gaps between adjacent turns of the wire 15 (FIG. 3) of electrode 14 to reach the electrolytic layer 12 and be absorbed by it. A voltage is applied between the two electrodes 14, 16 to pass a current through the electrolytic layer that electrolyzes the absorbed moisture to turn it into hydrogen and oxygen gas (actually into H and OH). The amount of current indicates the amount of moisture absorbed by the electrolytic layer, and therefore the amount of moisture in the surrounding environment. The electrolytic layer 12 can consist of a sheet of Nafion which is a sulfonated flourocarbon polymer that is highly stable.

The electrolytic layer 12 can swell and contract as it absorbs and loses moisture. Other parts of the device also can expand and contract with temperature changes. All during such expansion and contraction, it is important to maintain good contact between each of the primary electrodes 14, 16 and all areas of the electrolytic sheet 12 that they lie against. The slot 20 (FIG. 1) in the tubular frame 18 permits such contraction and expansion. In constructing the device, the tubular frame 18 is initially compressed to at least partially close the slot. The foil inner electrode 16 and electrolytic layer 12 are each wrapped tightly about the compressed tubular frame, and the wound wire outer electrode 14 is tightly wound about the electrolytic layer. The frame is then released so it can resiliently expand to maintain good contact between the electrodes and all areas of the electrolytic layer, despite slight expansion and contraction of the parts, such as the electrolytic layer 12 as it absorbs and loses moisture.

Figure 5:
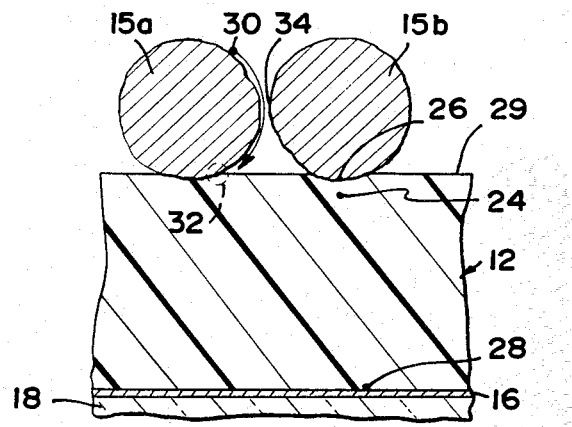
FIG. 5 is a view taken on the line 5—5 of FIG. 4.

The wound wire outer electrode 14 provides numerous closely-spaced contact locations with the electrolytic layer 12. This is desirable so that there is no water-containing portion of the layer which is far from a direct current flow between the electrodes 14, 16. Water that lies at a location, such as at 24 in FIG. 5, which is directly between contact points 26 and 28 where the electrodes contact the electrolytic layer 12, and which is close to the surface 29, will be electrolyzed within a few seconds when a moderate voltage is applied between the electrodes. Water lying a few millimeters away fron a direct line of current flow will take much longer to dissociate, such as perhaps a few hours when only a few parts per million of water is present. However, space must be left between adjacent turns of wire to provide openings through which water in the environment can reach the electrolytic layer 12 and be absorbed by it. These two requirements would appear to be in conflict.

It has been found that when two wire turns 15a, 15b are placed very close to one another, there is always a gap 34 between them, even if it is of microscopic size, and that this gap is sufficient to permit water in the environment to reach the underlying electrolytic layer 12. It is believed that this occurs by water molecules initially reaching the surface of a wire, such as at 30, and migrating along the surface of the wire to the location 32 where the surface of the wire first encounters the electrolytic material of the layer 12. A gap 34 must be present to permit such surface migration, but it need be only microscopically wide.

Figure 4:
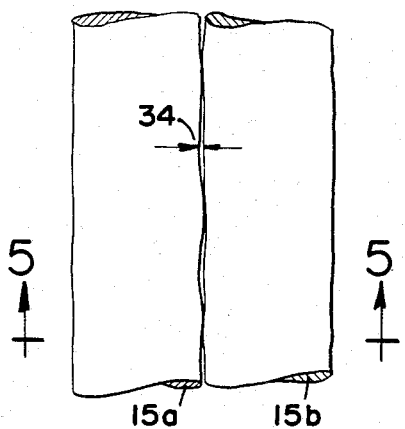
FIG. 4 is an enlarged view taken on the line 4—4 of FIG. 3.

When a wire is closely wound around the hygroscopic layer 12 so adjacent turns of wire substantially abut one another, the slight imperfections at the surface of the wire cause microscopic gaps, such as at 34 in FIG. 4, to be present between the two adjacent wire portions 15a, 15b along most of the lengths of the two wires. This gap 34 is much less than one-half the diameter of either wire (less than 15 mil for 30 mil diameter wire, a mil equalling 0.001 inch), but is sufficient to permit moisture to reach the electrolytic layer. Although adjacent turns of wire are used, it is possible to use a wire screen or the like where the wires lie flat or are partially curved. In any case, it is preferable that adjacent parallel wire segments lie very close together. The abutting relationship of the wires assures wire contact with the Nafion electrolytic layer without wide noncontact gaps of more than a fraction of a milimeter.

One problem that can arise is that the opposite ends 12e (FIG. 3) of the electrolytic layer cannot be easily covered by the coiled wire electrode 14. This is because at least some edge or end area of the layer must be left uncovered by wire to assure that the wire electrode 14 does not accidentally fall off the layer and touch the inner electrode 16. The uncovered layer end 12e is exposed to the environment so it absorbs moisture, but is not close to the outer electrode 14 so the moisture is not quickly removed by current passing between the primary electrodes 14, 16. As a result, it may take considerable time, such as hours, for a current passing through the wires to remove such moisture. Thus, the moisture at the end portions of the layer can reduce the accuracy of the instrument. To avoid such an end effect, applicant provides guard electrodes 42, 44 (FIG. 2) at locations closely beyond each end of the primary outer electrode 14.

Each guard electrode such as 42 (FIG. 3) includes a few turns of wire tightly wound about an end portion 12e of the electrolytic layer. However, the guard electrode 42 is insulated from the main electrode 14. When a voltage is applied between the primary electrodes 14, 16 to electrolyze moisture in the electrolytic layer portion between them, a voltage is also applied between the guard electrode 42 and the inner electrode 16. The current flowing through that part of the end portion 12e of the layer that underlies the guard electrode 42, electrolyzes the moisture lying directly under the guard electrode, to thereby remove this moisture at about the same rate as it is being removed from the regions underlying the primary outer electrode 14. Thus, moisture lying directly under the guard electrode 42 does not cause inaccuracy in the measurement of moisture lying under the primary electrode 14. Moisture lying on the end portion 12e of the layer beyond the guard electrode 42 is so far removed from the primary electrode 14 that it does not have any significant effect.

Figure 2:
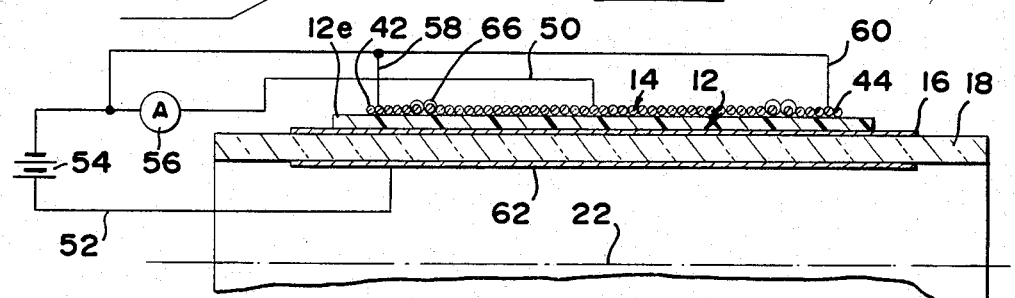
FIG. 2 is a sectional and diagramatic view of the sensor of FIG. 1, showing electrical circuitry connected thereto.

FIG. 2 illustrates electrical connections between the various electrodes of the hygrometer. A pair of conductors 50, 52 are connected to the primary electrodes 14, 16 (via foil edge 62), and an electrical source 54 and current measurement instrument or microammeter 56 are connected in series with the conductors 50, 52. Thus, the microammeter 56 measures the amount of current flowing through the electrolytic layer 12, in the portion thereof which lies under the outer electrode 14. Another pair of conductors 58, 60 are connected to the guard electrodes 42, 44 to apply the same voltage thereto that is applied to the primary outer electrode 14. However, current flowing through the guard electrodes 58, 60 does not affect the current measurement made by the microammeter 56.

Applicants have constructed a hygrometer of the type illustrated, using a cylindrical glass tube 18 in which a slit 20 was formed. The tube 18 was initially clamped to press the edges of the slit 20 together. A sheet of gold foil was applied by spraying adhesive on the tube and then wrapping the gold foil sheet tightly about the tube, with an edge 62 of the foil having been inserted through the slit 20 to provide electrical contact. An electrolytic sheet of Nafion was then wrapped around the foil. A coil of gold plated nickel wire of 30 mil diameter (one mil equals 0.001 inch) was then wound tightly around the electrolytic sheet or layer, and the ends of the wire covered with insulative tubing and secured to upstanding knobs 64 that had been attached to the tubular frame. The wire was wound so that adjacent turns of the wire lay against one another. The insulative tubing 66 (FIG. 3) had been placed on end portions of the wire to leave at least one full turn of tubing-covered wire at the ends of the main electrode 14 to insulate it from the guard electrodes 42, 44. The guard electrodes were separately wound and their ends attached to the knobs 64. After the wire ends were secured, the clamping force on the tubular frame was released, so the tube could spring back to its original slitted diameter to draw the coil of wire at 14 taut about the hygroscopic layer.

Thus, the invention provides a hygrometer of the type that uses a solid hygroscopic-electrolytic layer, which is reliable and accurate and which has a fast response time. The hygrometer includes a tubular frame with a slit therein about which the primary electrodes are wound with the electrolytic layer sandwiched between them, so the tubular frame can contract and expand to maintain reliable contact between the electrodes and electrolytic layer. One of the electrodes through which moisture reaches the electrolytic layer, includes parallel wires such as adjacent windings, which lie adjacent to one another with a gap between them much less than half each wire diameter, to provide contact with the layer at closely spaced locations, since it is found that moisture still easily passes through the electrode to the electrolytic layer. End effects are avoided by using guard electrodes at the ends to which voltages are applied, so the guard electrodes electrolyze moisture lying directly under them to avoid such moisture decreasing the sensitivity and accuracy of the hygrometer instrument.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A moisture sensor comprising:
a layer of hygroscopic electrolytic material having first and second opposite faces;
first and second electrodes laying respectively against said first and second faces of said layer;
said second electrode comprising a multiplicity of juxtaposed wire portions lying against said layer and extending parallel to one another, wherein each wire portion abuts the adjacent wire portion to leave only gaps primarily due to variations in wire width and wherein said second face of the electrolytic material is exposed to the ambient through said gaps.

2. The sensor described in claim 1 including:
a substantially cylindrical frame, said first electrode disposed about said frame, said layer of hygroscopic electrolytic material disposed about said first electrode, and said second electrode comprising a wire wound in a coil around said layer with adjacent turns of wire against one another and forming said wire portions.

3. A moisture sensor as defined in claim 2 wherein:
said second electrode is wound over only a middle portion of said hygroscopic-electrolytic layer to leave end portions thereof free of contact with said second electrode, but said first electrode lying against said end portions of said layer hygroscopic-electrolytic material against said first surface thereof;
a pair of guard electrodes at opposite end portions of said hygroscopic-electrolytic layer against said second surface thereof, said guard electrodes being free of direct electrical connection to said second electrode; and
a circuit which includes means for applying a voltage between said first and second electrodes, and for applying a voltage between each of said guard electrodes and said first electrode, and means for measuring current flowing between said first and second electrodes independently of current flowing between said guard and first electrodes.

4. A moisture sensor as defined in claim 3 wherein:
said cylindrical frame having means for permitting contraction and expansion of the frame, whereby to enable maintenance of tight contact of the electrodes with the hygroscopic electrolytic layer.

5. A moisture sensor as defined in claim 4 wherein said frame has a slit forming said means for permitting contraction and expansion, and said inner electrode comprises a foil of conductive material that has a portion which extends through said slit to lie within said frame and is connected to said means for applying a voltage.

* * * * *